United States Patent [19]

Dalton et al.

[11] 4,251,393

[45] Feb. 17, 1981

[54] ATTRITION RESISTANT CATALYSTS

[75] Inventors: Charles A. Dalton; William E. Slinkard, both of Corpus Christi, Tex.

[73] Assignee: Celanese Corporation, New York, N.Y.

[21] Appl. No.: 42,754

[22] Filed: May 29, 1979

[51] Int. Cl.$^3$ .......................... B01J 21/00; B01J 23/16
[52] U.S. Cl. .................................... 252/443; 252/456; 252/458; 252/477 R
[58] Field of Search .................. 252/456, 446, 477 R, 252/443; 562/547

[56] References Cited

U.S. PATENT DOCUMENTS

| | | | |
|---|---|---|---|
| 2,941,958 | 6/1960 | Connor, Jr. et al. | 252/449 |
| 4,077,912 | 3/1978 | Dolhyj et al. | 252/461 |
| 4,107,085 | 8/1978 | Sasaki et al. | 252/456 X |
| 4,157,315 | 6/1979 | Michels et al. | 252/477 R |

Primary Examiner—Carl F. Dees
Attorney, Agent, or Firm—Linn I. Grim

[57] ABSTRACT

Catalysts having improved attrition resistance are produced by incorporating a substantially uniform appearing coating of completely calcined, catalytically active oxide material onto an inert porous support containing sorbed aqueous silica sol. Such catalysts are useful in the gas phase oxidation of unsaturated aldehydes to unsaturated acids, especially acrolein to acrylic acid.

7 Claims, 2 Drawing Figures

ATTRITION RESISTANT CATALYSTS

BACKGROUND OF THE INVENTION

The present invention relates to improved fixed bed attrition resistant catalysts and to their use in exothermic chemical processes, such as gas phase oxidation of acrolein to acrylic acid.

Catalysts useful for exothermic reactions have been prepared conventionally as pills or tablets having essentially a uniform catalyst composition throughout. Catalysts prepared in this manner can be extremely active when used in fixed bed exothermic oxidation reactions. In some cases however, "hot spots" can cause large amounts of undesirable by-products to be produced, due to the fact that the heat generated by the reaction cannot be dissipated efficiently by normal heat transfer techniques.

One method which has been tried to overcome this difficulty is to use inert catalysts supports which contain the catalytically active materials coated on the support surface. This reduces the amount of catalytically active material in the reactor and cuts down undesirable catalytic activity, thereby better controlling the heat produced in the reaction and substantially eliminating "hot spots". However, such coated catalysts often exhibit a significant degree of attritability, i.e., they break down in use to give significant amounts of catalyst fines. As these fine particles accumulate in the reactor, high pressure drops develop. Once the pressure reaches an unacceptably high level, the reaction must be stopped even though the catalyst may still retain good activity.

Attempts have been made in the past to provide active supported catalysts having acceptable attrition resistance. For example, U.S. Pat. No. 3,341,471 describes attrition resistant solid catalysts prepared by mixing finely divided catalytic active components with an aqueous silica sol, forming a paste or slurry, drying the mixture, heat-treating the finished finely divided catalyst and then pelletizing, yielding a catalyst having catalytically active material essentially uniformly distributed throughout the pellets. This catalyst, however, when used in a fixed bed reactor in the oxidation reaction of olefins to oxygenated hydrocarbons, among other reactions, still has a tendency to result in undesirable "hot spots".

U.S. Pat. No. 4,077,912 describes a procedure for producing a coated catalyst said to have good attrition resistance which involves wetting a porous inert support with "an inorganic or organic liquid", water and petroleum ether being specifically disclosed, in such a manner that the resulting wetted support does not have the appearance of free liquid in contact with the support particles, then gently agitating a catalytically active material onto the surface. This patent also identifies many other U.S. patents which describe various techniques of producing supported catalysts. U.S. Pat. No. 3,644,059 describes the catalytically active oxide material which can be utilized in producing the catalysts of the present invention.

None of the aforementioned patents describe the attrition resistant catalysts of the present invention, nor do they describe the present inventive method of preparing such catalysts.

SUMMARY OF THE INVENTION

It has now been discovered that catalysts for the oxidation of unsaturated aldehydes to their corresponding unsaturated acids which comprise a catalytically active material contained on an inert porous support and which exhibit improved attrition resistance can be prepared by coating a finely divided completely calcined, catalytically active oxide material onto the surface of an essentially inert porous support which has previously been wetted with an aqueous silica sol containing from about 20 to about 40 weight percent silica so as to provide a coated catalyst having a substantially uniform appearance.

The amount of aqueous silica sol used to wet the inert porous support will be an amount sufficient to moisten the support up to the maximum amount the support can sorb and yet result in a moistened support which does not have the appearance of free liquid in contact with the support particles.

The amounts of silica sol can be defined in terms of weight percent moisture ratio i.e. the percentage ratio of the weight of silica sol to the combined weights of aqueous silica sol and catalytically active oxide material. For silicon carbide support, the moisture ratio, preferably ranges from about 15 percent to about 51 percent. After the catalytically active oxide coating has been applied to the wetted inert porous support generally by thorough agitation, the resultant catalyst is dried.

A catalyst produced in accordance with this invention was found to have an attrition loss of fines through a 20 mesh screen not exceeding about 5 weight percent when 100 grams of dried catalyst was rotated in a stainless steel cylindrical drum of the type described hereinafter and shown in the drawing, at 60 revolutions per minute for 1.5 minutes at room temperature.

DETAILED DESCRIPTION OF THE INVENTION

A wide variety of materials known in the art can be used to make the catalysts of the present invention. Normally, two discrete parts—an essentially inert porous support and an active catalytic material—will be employed.

The essentially inert porous support may be selected from a wide variety of known materials which have an outer surface capable of holding finely divided catalytically active material and which are also capable of being wetted with an aqueous silica sol.

Included among the essentially inert porous supports which can be used in preparing the catalysts of the present invention are alumina (preferably as Alundum, a pure crystalline grade of aluminum oxide), silica, alumina-silica, silicon carbide, titania and zirconia. Silicon carbide is especially preferred.

The aqueous silica sol used as the wetting agent for the preparation of the catalysts of this invention is available commercially, or if desired can be derived from water glass or other silicon compounds. The amount of silica in the aqueous silica sol can range from about 20 to about 40 weight percent, based on the total weight of the silica sol, and preferably will range from about 30 to about 40 weight percent, again based on the total weight of the silica sol.

The amount of aqueous silica sol sorbed on the essentially inert porous support can be determined using a percentage of moisture ratio calculated in the following manner:

% Moisture Ratio =

$$\frac{\text{weight liquid aqueous silica sol}}{\text{weight catalytically active oxide material} + \text{weight liquid aqueous silica sol}} \times 100$$

The moisture ratio can range from about 15% to about 51%, and preferably will range from about 25% to about 45%, depending on the essentially inert porous support and catalytically active oxide material chosen. The amount of aqueous silica sol in the support should not exceed the maximum amount which the support can sorb. If an excess of silica sol is present, the catalytically active oxide material to be coated onto the support can agglomerate and the resulting catalyst will be undesirable for use in the oxidation process in regard to high attrition and low oxidation activity.

The second component of the catalysts of the present invention is a catalytically active oxide material for the oxidation of olefinically unsaturated aldehydes to the corresponding unsaturated acids. The term "olefinically unsaturated aldehydes" as employed herein is meant to include aldehydes containing between 3 and 5 carbon atoms as the preferred class of starting materials. The preferred catalysts generally contain combinations of alkali metals, alkaline earth metals, V, Cr, Mo, W, Mn, Fe, Co, Ni, Cu, Zn, In, Tl, Sn, Sb, Bi, P and As. Preferred among these catalytically active materials are Mo, V, W and Mn. The most preferred combinations of catalytically active oxide materials for the oxidation of acrolein to acrylic acid are described in U.S. Pat. No. 3,644,509 assigned to Celanese Corporation, entitled "Oxidation of Unsaturated Aldehydes to the Corresponding Acids", issued Feb. 22, 1972. These most preferred combinations can be represented by the empirical formula:

$$Mo_a V_b W_c Mn_d O_e$$

wherein the atomic ratio of Mo:V:W:Mn:O in said combination is such that when a is 12, b is from 0.5 to 12, preferably 1 to 6, c is 0.1 to 6, preferably 0.3 to 3, d is 0.5 to 20, preferably 1 to 12 and e is a number which indicates that sufficient oxygen is present to satisfy the valence requirements of the other elements.

The catalytically active materials of the above empirical formula may be regarded as a mixture of oxides of the various metals and/or mixtures of heteropolyacid salts of the various metals. The catalytically active material may be prepared by any conventional method, such as by mixing aqueous solutions of water soluble compounds of the metals and then evaporating the water to leave a dry cake which is calcined, preferably after being reduced to powder. Suitable water soluble compounds useful in the preparation of a catalytically active material include ammonium paramolybdate, ammonium metavanadate, ammonium paratungstate, manganous acetate, ammonium metatungstate, orthotungstic acid, metatungstic acid, molybdic acid, molybdenum trioxide, manganous benzoate and manganous nitrate. When the catalytically active material is to be used in the oxidation of unsaturated aldehydes such as acrolein to acrylic acid, it is preferred that it be prepared by (1) forming an aqueous solution of an ammonium molybdate, an ammonium tungstate, an ammonium vanadate and a water soluble manganese salt of an inorganic or organic acid (2) evaporating the liquid to obtain a solid which is (3) then completely calcined.

The catalytically active oxide materials are completely calcined in air or other gases containing molecular oxygen at temperatures in the range from about 360° C. to about 420° C., preferably from about 365° C. to about 405° C. for a period of time sufficient to eliminate substantially all volatile materials and to give optimal catalytic performance. The calcination should be conducted for at least 3 hours, and preferably for 5 hours. If the catalytically active oxide materials are not completely calcined, the attrition index of the catalyst will, generally, not fall within the desired special attrition index of below 5 weight percent as defined below.

The finely divided calcined catalytically active oxide materials may be coated onto the wetted support by any suitable means, for example, by tumbling in a rotating drum at room temperature. The catalytically active oxide material is added to the rotating drum until the desired amount of catalytically active oxide is placed onto the support or until no more is taken up on the support.

The amount of catalytically active oxide materials coated on the support can range from about 10 to about 50 weight percent, preferably from about 10 to about 30 weight percent of the total catalyst. The finished catalyst particles which have a uniformly appearing coating, are then dried. The purpose of drying the coated catalyst is to remove the water contained therein. The coated catalyst can be dried at temperatures in excess of 100° C. to as high as 180° C., depending on the relative humidity and catalyst depth for a period of time sufficient to remove the water. The preferred drying temperatures can range from about 140° C. to about 160° C. for about 16 to about 18 hours. The foregoing steps are carried out such that the special attrition index of the finished catalyst determined as described before, is no higher than 5 weight percent.

The dried catalyst is evaluated for particle integrity by conducting a special attrition test. The results of the special attrition test is defined in this specification and claims as a "special attrition index" in terms of weight percent. The attrition test procedure requires that the sample be thoroughly dried by placing it in a desiccator under vacuum over Drierite (anhydrous calcium sulfate dessicant) for a sufficient period of time, for example 18 to 20 hours prior to testing, the catalyst sample is sieved on a 20 mesh screen to remove any fine particles. 100 grams of sieved catalyst is rotated in a stainless steel cylindrical drum (6 inches in length and 10 inches in diameter) at 60 revolutions per minute for 1.5 minutes at room temperature. The drum has a radial baffle attached to one of its cylinder faces and the baffle extends 5.5 inches in the axial direction. Additionally the baffle is attached to the inner cylinder wall and extends 2 inches in the radial direction. The catalyst is removed from the drum and the fine particles are sieved through a 20 mesh screen. The material remaining on the screen is weighed. The special attrition index is calculated as follows:

$$\text{special attrition index (weight percent)} = \frac{\text{original weight} - \text{final weight retained on screen}}{\text{original weight}} \times 100$$

The special attrition index for the catalyst of this invention should not exceed 5 weight percent according to the above-described attrition test.

The drawings are a diagrammatic illustration of the stainless steel cylindrical drum used to evaluate particle integrity of the catalyst in the attrition test of this invention.

Figure 1:
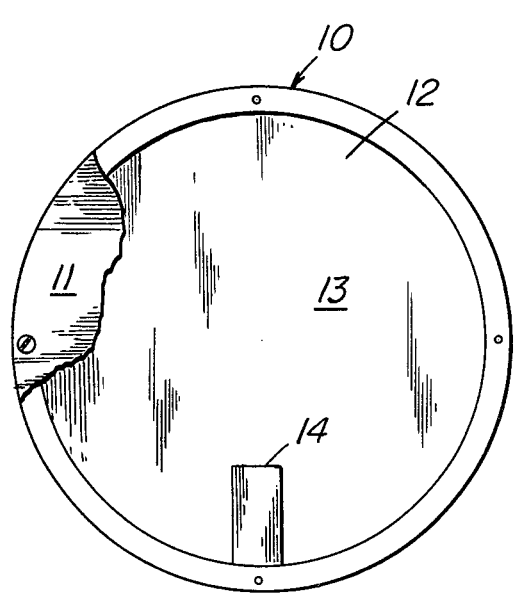
FIG. 1 is a front view of the open cylindrical drum with an indication of a fragmentary portion of the front plate 11.
Figure 2:
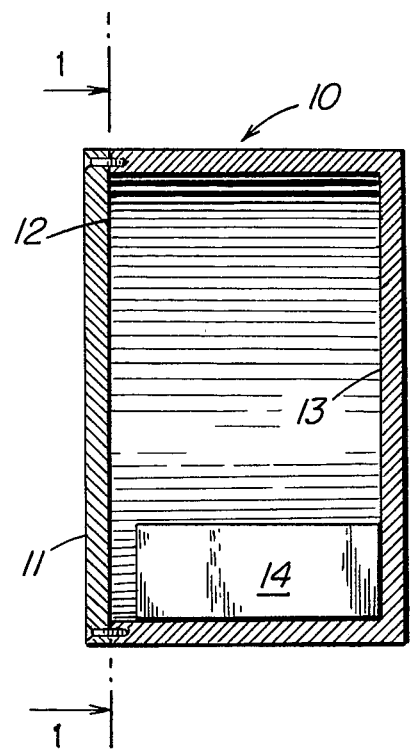
FIG. 2 is a cross section view of the cylindrical drum with cover plate in place.

Referring to the drawings, the overall stainless steel cylindrical drum 10 (6 inches in inner length and 10 inches in inside diameter) contains a removable cover 11 on cylinder face 12. The other cylinder face 13 has a radial baffle 14 attached thereto. The baffle 14 extends 5.5 inches in the axial direction from the inner cylinder face 13. The baffle 14 also is attached to the inner cylinder wall, and is 2 inches wide extending in the radial direction. There are means, not shown, to rotate the stainless steel cylindrical drum 10 at varying speeds.

Catalysts prepared in accordance with this invention can be utilized in the production of unsaturated carboxylic acids by the oxidation of unsaturated aldehydes, and especially in the oxidation of acrolein to acrylic acid. Such processes can be carried out continuously in a fixed bed using the catalysts of this invention. Portions of the reactants which do not undergo reaction may be recycled, if desired. The temperatures employed in such oxidation processes are preferably between about 250° C. to about 420° C., and preferably are in the range from about 270° C. to about 370° C.

The pressures employed in such processes may be subatmospheric, atmospheric or superatmospheric. Usually pressures ranging from 0.5 to 3.0 atmospheres will be utilized, although pressures up to 10 atmospheres and higher may be employed. The contact time of the reactants with catalyst under the above-described reaction conditions is generally between 0.3 and 15 seconds, and preferably a relatively shorter time, e.g., from 0.5 to 10 seconds. By contact time as used herein is meant the contact time adjusted to 25° C. and atmospheric pressure (conditions denoted by NTP). Thus the contact time is calculated by dividing the volume of the catalyst bed (including voids) by the volume per unit time flow rate of the reactants at NTP.

The oxygen necessary as a reactant in such oxidation processes may be from any molecular oxygen-containing gas such as concentrated molecular oxygen or air. For example, the molecular oxygen-containing gas may be one wherein molecular oxygen is mixed in varying amounts with an inert diluent gas such as nitrogen, argon or carbon dioxide. The unsaturated reactant may be premixed with the oxygen-containing gas before introduction to the reaction zone or the reactants may be introduced separately into the reaction zone. Also the unsaturated aldehyde and/or molecular oxygen may be introduced into the reaction zone at one or a plurality of points along the length of the reaction zone. The reactants may be pretreated before entering the reaction zone; this includes pretreatments to remove undesirable components.

In conducting the oxidation reaction, the gaseous feed mixture should generally contain from 0.5 to 6 moles of oxygen per mole of the unsaturated aldehyde although the preferred range is from 0.8 to 4.0 moles per mole. Water is also desirably present in the gaseous feed in amounts of from 1 to 25, preferably 2 to 20 moles per mole of unsaturated aldehyde. In addition to water, diluents which are gaseous under the reaction conditions and are relatively inert, may be introduced into the system. Suitable diluents include nitrogen, flue gas, $CO_2$ and paraffinic hydrocarbons.

The catalysts and process for their preparation of this invention are illustrated in the following Examples.

EXAMPLE 1

Silicon carbide spheres of 3/16 inch diameter having a surface area of 0.003 $m^2$/g, a packing density of 40 pounds per cubic foot, a water absorbtivity of 54 weight percent, a total porosity (by mercury penetration) of 0.53 cc/gm and a median pore diameter of 78 micrometers were used as the support. 700 grams of these spheres were weighed in a 2 gallon (7-inch diameter) polyethylene jar which was then placed on a jar mill roller (Norton Jar Mill Roller, Model 753 RMV), rotating at 60 revolutions per minute. While the jar was rotating, 90 grams of an aqueous, ammonia-stabilized silica sol containing 40% by weight of silica (du Pont Ludox As-40) stabilized to a pH of 8.0 with ammonium hydroxide, was sprayed by a common household sprayer onto the silicon carbide spheres. The moistened spheres were tumbled for 5 minutes to distribute the silica sol throughout the spheres after which they were transferred to a "V" blender (Patterson Kelley Co. liquid solids 2 quart "V" type).

A calcined powder was prepared by mixing solutions of ammonium paramolybdate (84.8 grams in 200 ml of water), ammonium metavandate (14.0 g in 200 ml of water), ammonium paratungstate (12.2 grams in 100 ml of water) and manganous acetate tetrahydrate (90 grams in 200 ml water). The resulting suspension was evaporated to dryness at 120° C. in a stream of air, and the dried powder was heated for 5 hours at 385° C. in an oven with forced air circulation. The powder can be represented by the empirical formula:

$$Mo_{12}V_3W_{1.2}Mn_3O_{53}$$

Calcined powder in an amount of 90 grams, was added to the "V" blender containing the wetted silicon carbide spheres and the blender was rotated 8 revolutions. An additional 90 grams of calcined powder were added to the blender and the blender was rotated for 8 minutes. The moisture ratio in this catalyst preparation was 33 weight percent. The coated catalyst having a substantially uniform appearance, e.g. having substantially no uncoated support particles or clumps of unsupported catalyst powder, was removed from the blender and spread evenly onto trays (20 inches×22 inches). The trays containing the catalyst, were placed in an oven for drying overnight (~16 hours) at 140° C. After cooling, the catalyst was ready for use. The attrition loss (hereinafter called special attrition index) of the dried catalyst through a 20 mesh screen when rotated in a stainless steel drum (6 inches in length and 10 inches diameter) containing a baffle as heretofore described, at 60 revolutions per minute for 1.5 minutes was 2 weight percent.

The catalyst of Example 1 when used in the oxidation of acrolein to acrylic acid produced yields of acrylic acid from 92 to 95% at acrolein conversions of 99.0 to 99.8% in a fixed bed at contact times (NTP) of 1.9–2 seconds, reaction temperatures of 290° C. to 310° C. at 15 psig pressure. The reactor feed composition was as follows:

| | |
|---|---|
| water to acrolein | 9.1/1 |
| oxygen to acrolein | 1.3/1 |

-continued

| nitrogen to acrolein | 11.4/1 |

In these examples the terms "conversion" and "yield" are defined as follows:

$$\text{conversion \%} = \frac{\text{moles acrolein converted}}{\text{moles acrolein fed}} \times 100$$

$$\text{yield mole \%} = \frac{\text{moles acrylic acid produced}}{\text{moles acrolein fed}} \times 100$$

EXAMPLE 2

The catalyst preparation of Example 1 was repeated except that 72 grams of the 40% by weight silica sol solution were used such that the moisture ratio used was 28.6 weight percent. The special attrition index was 4 weight percent. In the oxidation of acrolein to acrylic acid using the same conditions as used for the catalyst of Example 1, acrylic acid yields of 93% were obtained at an acrolein conversion of 99.8% at a reaction temperature of 297° C.

EXAMPLE 3

The catalyst preparation of Example 2 was repeated except the tumbling time and the drying temperature were different. One 90 gram increment was tumbled with the silicon carbide for one minute and the other 90 gram increment was added immediately thereafter and the catalyst tumbled for 3 minutes. The drying temperature was 125° C. The special attrition index was 10 percent.

When compared to the catalyst prepared in Example 2 under the same conditions except for the length of tumbling time and drying temperature, an improved catalyst, i.e. having a special attrition index of 5 weight percent or below, will not be produced if the tumbling time is not sufficient. Thus, tumbling time should be great enough to result in a special attrition index not exceeding 5 weight percent.

EXAMPLE 4

The catalyst preparation of Example 1 was repeated except water was used instead of aqueous silica sol. The special attrition index was 10%. This represents a catalyst made in a manner similar to U.S. Pat. No. 4,077,912 which utilizes water as a wetting agent for the support.

EXAMPLE 5

In a catalyst preparation duplicating Example 1 except the silicon carbide was soaked in aqueous silica sol instead of spraying, the resulting catalyst was unsatisfactory for use because the special attrition index was well above 10 weight percent.

The catalyst produced from silicon carbide spheres soaked with silica sol such that the latter can be observed as free liquid on the support particles indicates that excess silica sol is present on the support, resulting in agglomeration on tumbling.

EXAMPLE 6

As a comparative example to Example 1, 100 grams of silicon carbide spheres, as described in Example 1, were placed into a 500 cc plastic bottle. The 500 cc plastic bottle containing the silicon spheres was placed in a 2 gallon plastic jar and rotated on a Norton Jar Mill at 60 revolutions per minute. The silicon carbide spheres were sprayed with 10 grams of 40 percent silica sol (Ludox AS-40) and tumbled for 5 minutes to distribute the silica sol throughout the spheres. A first increment of 12.5 grams of a partially calcined (350° C. for 3 hours) catalytically active powder (precursor of the catalytically active powder of Example 1) was tumbled for 30 seconds onto the silicon carbide spheres. A second increment of 12.5 grams of the partially calcined catalytically active powder was tumbled for 2 minutes onto the silicon carbide spheres. The resulting catalyst product was calcined 5 hours at 385° C. The special attrition index of this catalyst was 11 weight percent while the yields of acrylic acid decreased to 90% at 99% acrolein conversion at a reaction temperature of 277° C.

EXAMPLE 7

The catalyst preparation of Example 6 was repeated except the aqueous silica sol used contained 20% instead of 40% by weight of silica and the first increment of partially calcined catalytically active powder was tumbled for one minute and the second increment of partially calcined catalytically active powder was tumbled for two minutes. The special attrition index of the finished catalyst was 7 weight percent while the activity of the catalyst and yields of acrylic acid were similar to those of Example 6 providing yields of acrylic acid of 90% at 99% acrolein conversion at a reaction temperature of 273° C.

EXAMPLE 8

As a comparative example to Example 1, a catalyst was prepared utilizing uncalcined catalytic powder (compared to calcined powder) to coat the wetted silicon carbide support followed by calcination of the coated powder on the support. The equipment used was the same as Example 1 and the procedure of Example 1 was substantially followed with a few exceptions.

700 grams of silicon carbide spheres as described in Example 1 were wetted by spraying with 90 grams of silica sol containing 40% silica (Ludox AS-40). The moistened spheres were tumbled in a jar mill roller for 5 minutes after which they were transferred to a "V" blender. Uncalcined powder which was the precursor of the calcined powder of Example 1 in an amount of 100 grams was added to the "V" blender containing the wetted silicon carbide spheres and the blender was rotated 8 revolutions. A second increment of 100 grams of uncalcined powder was added to the blender and rotated for 8 revolutions. A third and final increment of 100 grams of uncalcined powder was added to the blender and rotated for 5 minutes. The moisture ratio was 23.1 weight percent. The coated catalyst having a substantially uniform appearance was removed from the blender and spread evenly onto trays (20 inches × 22 inches). The trays containing the catalyst were placed in an oven for calcination for 5 hours at 385° C. The special attrition index of the calcined catalyst was 23–26 weight percent. Using similar reaction conditions of Example 1, except for reaction temperatures of 322° C., and contact time of 2.3 seconds, the acrolein conversion was 97% and acrylic acid yield of 87%.

The catalyst of Example 8 required higher temperatures to provide acrolein conversions of 97–98% than do the catalysts of this invention as demonstrated in Example 1. Additionally, the high special attrition index of the catalysts of Example 8 indicates that in the oxidation reaction, higher pressures would be reached in a shorter period of time under similar reaction conditions because of the build up of fines than would be required by the catalyst of Example 1 which has a special attrition index of 2 weight percent. Thus, the useful life of the catalyst of Example 8 would be shorter than that of the catalyst of Example 1 representing the catalysts of the present invention.

As indicated by the foregoing working examples, certain essential requirements must be met in order to obtain the improved catalysts of the present invention. In turn such catalysts can lead to improved economies in processes such as the oxidation of aldehydes to the corresponding acids.

Initially, in aldehyde to acid oxidation processes, it is desirable that the catalyst have special attrition index not exceeding 5 weight percent according to the attrition test described herein. Catalysts having special attrition index in excess 5 weight percent will, if used, significantly increase the pressure drop in the reactor over a relatively short period of time and hence will have a shorter useful life. When the pressure becomes too high, the reaction must be discontinued and the catalyst removed which disrupts production. It should be noted that, as in Examples 6 and 7, if the catalyst powder is not completely calcined prior to its addition to the porous support, or as in Example 8, if the catalyst is not calcined until after the powder has been added to the silica sol wetted support, the catalyst obtained generally has a special attrition index in excess of 5 weight percent. Further, yields of acrylic acid from acrolein are reduced in a process in which catalysts have been calcined after the coating operation compared to the yields obtained using the catalysts of this invention under similar oxidation conditions.

Additionally, as shown in Example 4, if water is substituted for aqueous silica sol, the resulting catalysts have higher attrition losses than the corresponding catalysts prepared using aqueous silica sol.

The catalytically active oxide powder must be uniformly coated onto the porous support. To obtain uniform coating, the aqueous silica sol must be contacted with the porous support such that no free liquid can be observed in contact with the support particles i.e. the latter are substantially dry-appearing. Spraying the aqueous silica sol onto the porous carrier and tumbling appears to provide an acceptable wetted support. If the aqueous silica sol is not distributed properly as indicated by the appearance of free liquid on the support particles, the catalytically active oxide powder will agglomerate and not provide a catalyst having improved physical strength.

Finally, the amount of tumbling which will be employed can vary depending on the type of support and catalytically active oxide powders used. Example 3 illustrates that insufficient tumbling of the catalytically active oxide powders onto the support will not provide the improved result achieved in the present invention. In general, however, if 100 grams of the dried catalyst of this invention has achieved an attrition index loss not exceeding 5 weight percent as measured by the above described attrition test, the catalyst ingredients have been tumbled together for a sufficient period of time.

What is claimed is:

1. An improved attrition resistant catalyst comprising:
   (A) an essentially inert porous support capable of holding finely divided catalytically active material on its outer surface, said support wetted with a sufficient amount of aqueous silica sol containing from about 20 to about 40 weight percent silica to provide a support which contains up to the maximum amount of silica sol said support can sorb but does not have the appearance of liquid on the outer surface of said support; and
   (B) a finely divided catalytically active oxide material for the oxidation conversion of olefinically unsaturated aldehydes to the corresponding unsaturated acids, completely calcined at temperatures in the range from about 360° C. to about 420° C.;
   said finely divided catalytically active oxide material having been coated onto the surface of said wetted porous support in a manner to provide a uniform-appearing coating and the resulting catalyst dried, said catalyst having a special attrition index not exceeding 5 weight percent.

2. The catalyst of claim 1 wherein the inert porous support is silicon carbide, the aqueous silica sol used contains 30 to 40 weight percent of silica, the amount of catalytically active oxide material ranges from about 10 to about 50 weight percent based on the total catalyst and the moisture ratio ranges from about 15 to about 51 percent.

3. The catalyst of claim 2 wherein the catalytically active oxide material is calcined at temperatures in the range from about 365° C. to 405° C., the amount of catalytically active oxide material ranges from about 10 to 30 weight percent based on the total catalyst and the moisture ratio ranges from about 25 to about 45 percent.

4. The catalyst of claim 2 wherein the catalytically active material has the empirical formula:

$$Mo_aV_bW_cMn_dO_e$$

wherein the atomic ratio of Mo:V:W:Mn:O being such that when a is 12, b is 0.5 to 12, c is 0.1 to 6, d is 0.5 to 20 and e is a number which represents that sufficient oxygen is present to satisfy the valence requirements of the other metals.

5. The catalyst of claim 4 wherein the formula of said catalytically active material is such that when a is 12, b is 1 to 6, c is 0.3 to 3.0, d is 1 to 12, and e is a number which represents that sufficient oxygen is present to satisfy the valence requirements of the other metals.

6. An improved attrition resistant catalyst prepared by the steps comprising:
   (1) wetting uniformly an essentially inert support capable of holding finely divided active material on its surface, with a sufficient amount of aqueous silica sol containing from about 20 to about 40 weight percent silica to provide a support which contains up to the maximum amount of aqueous silica sol said support can sorb without having the appearance of liquid on the surface of said support;
   (2) coating the outer surface of said inert porous support with a finely divided catalytically active oxide material for the oxidation of olefinically unsaturated aldehydes to the corresponding unsaturated acids, said active oxide material having been completely calcined at temperatures in the range from about 360° C. to about 420° C., said finely divided catalytically active oxide coated onto the surface of said wetted porous support in a manner to provide a uniformly appearing coating; and
   (3) drying the resultant catalyst.

7. A process for producing an improved attrition resistant catalyst comprising the steps of:

(1) wetting uniformly an essentially inert support capable of holding finely divided active material on its surface, with a sufficient amount of aqueous silica sol containing from about 20 to about 40 weight percent silica to provide a support which contains up to the maximum amount of aqueous silica sol said support can sorb without having the appearance of liquid on the outer surface of said support;

(2) coating the outer surface of said inert porous support with a finely divided catalytically active oxide material for the oxidation of olefinically unsaturated aldehydes to the corresponding unsaturated acids, said active oxide material having been completely calcined at temperatures in the range from about 360° C. to about 420° C., said finely divided catalytically active oxide coated onto the surface of said wetted porous support in a manner to provide a uniformly appearing coating; and (3) drying the resultant catalyst.

* * * * *